United States Patent [19]
Johnson et al.

[11] Patent Number: 5,447,069
[45] Date of Patent: Sep. 5, 1995

[54] APPARATUS AND METHOD FOR ULTRASONICALLY MEASURING THE POISSON'S RATIO OF THIN LAYERS

[75] Inventors: Eric C. Johnson, Hawthorne, Calif.; Jessica D. Pollchik, Huntsville, Ala.; Juliet N. Schurr, Torrance, Calif.

[73] Assignee: The Aerospace Corporation, El Segundo, Calif.

[21] Appl. No.: 86,075

[22] Filed: Jun. 29, 1993

[51] Int. Cl.⁶ .............................................. G01N 29/00
[52] U.S. Cl. ........................................ 73/602; 73/620; 73/624
[58] Field of Search ............................ 73/602, 620, 624

[56] References Cited

U.S. PATENT DOCUMENTS

| | | | |
|---|---|---|---|
| 4,821,574 | 4/1989 | Takamizawa | 73/602 |
| 5,167,157 | 12/1992 | Wertz et al. | 73/627 |
| 5,243,855 | 9/1993 | Steiger et al. | 73/153 |
| 5,305,239 | 4/1994 | Kinra | 73/602 |

Primary Examiner—Richard E. Chilcot, Jr.
Assistant Examiner—Max H. Noori
Attorney, Agent, or Firm—William J. Burke; Derrick M. Reid

[57] ABSTRACT

An untrasonic technique is presented which permits accurate measurement of the Poisson's ratio for a specimen which exists as a thin (<10 mil) layer. This technique measures resonance and should prove especially useful in situations where a bulk specimen is either not readily available or would not properly reflect the properties of the material when configured as a thin layer. A detailed discussion of the theory underlying the technique is included. The technique is then used to determine the values of Poisson's ratio of three thin specimen materials. These values were then contrasted to those of the bulk specimens obtained in a more conventional manner. The technique as presented could be extended for a number of applications, including the cure monitoring of adhesives.

20 Claims, 3 Drawing Sheets

APPARATUS AND METHOD FOR ULTRASONICALLY MEASURING THE POISSON'S RATIO OF THIN LAYERS

STATEMENT OF GOVERNMENT INTEREST

The invention was made with Government support under Contract No. F04701-88-C-0089 awarded by the Department of the Air Force. The Government has certain rights in the invention.

BACKGROUND OF THE INVENTION

1. FIELD OF THE INVENTION

The present invention relates to the determination of Poisson's ratio, particularly for thin layers.

2. DESCRIPTION OF THE PRIOR ART

It is known that the Poisson's ratio for a material can be determined from the ratio of the acoustic shear velocity to the longitudinal velocity. These velocities can often be easily measured using conventional ultrasonic time-of-flight techniques. Over the years, however, difficulties associated with making velocity measurements on thin attenuative specimens have forced ultrasonic researchers to become more innovative. For example, in an early effort to measure the velocity of both transverse and longitudinal waves in a buna-N vulcanizate as a function of temperature, A. W. Nolle and P. W. Sieck, J. Appl. Phys., Vol. 23, 888, (1952) employed a method involving the use of solid transmission media to conduct pulses into a thin flat specimen. The error associated with the acoustic measurement, however, was estimated in the report to be as high as 5% and 10% for the longitudinal and shear wave data, respectively. J. R. Cunningham and D. G. Ivey, J. Appl. Phys., Vol. 27,967 (1956) improved upon the aforementioned technique by incorporating a double acoustic path comprised of two separate specimens. Again, however, a number of experimental difficulties (e.g., producing uniform sample bondlines) contributed to significant measurement error. More recently, V. K. Kinra and V. Dayal, Experimental Mechanics, Vol. 28, 289 (1988) report combining standard FFT methods with conventional ultrasonics to measure the longitudinal phase velocity in specimens of submillimeter thicknesses. Their report includes a brief summary and comparison of their technique to those recently developed by others including the resonance method of F. H. Chang, J. C. Couchman and B. G. W. Yee, J. Comp. Mat., Vol. 8, 356 (1974) and the phase insensitive tone-burst spectroscopic method of J. S. Heyman J. Acoust. Soc. Amer., Vol. 64, 243 (1968) [5]. A primary object of the present invention is therefore to develop a schematic for making velocity measurements on thin attenuative specimen.

SUMMARY OF THE INVENTION

A simple ultrasonic resonance technique which permits measurement of the Poisson's ratio of thin adhesive material specimens is presented. The acoustic shear and longitudinal velocity are also determined. This technique is characterized by a number of advantages. The Poisson's ratio measurement accuracy is limited only by that of the resonant frequency; the Poisson's ratio is independent of the thickness of the specimen. The same specimen and transducer pair are used to determine both the shear and longitudinal response. A fluid medium is employed to couple sound into the specimen, thereby eliminating many of the problems associated with the bonding of transducers.

DETAILED DESCRIPTION OF THE PREFERRED EMBODIMENT

The present invention is directed toward making Poisson's ratio measurements on thin material specimens, where thin is understood to be on the order of several mils. The Poisson's ratio for a material can be determined through measurement of its acoustic velocities using the relation:

$$\sigma = \frac{c_l^2 - 2c_s^2}{2c_l^2 - 2c_s^2}, \tag{1}$$

where $\sigma$ is the Poisson's ratio and $c_l$ and $c_s$ are the longitudinal and shear acoustic velocities, respectively.

Figure 1:
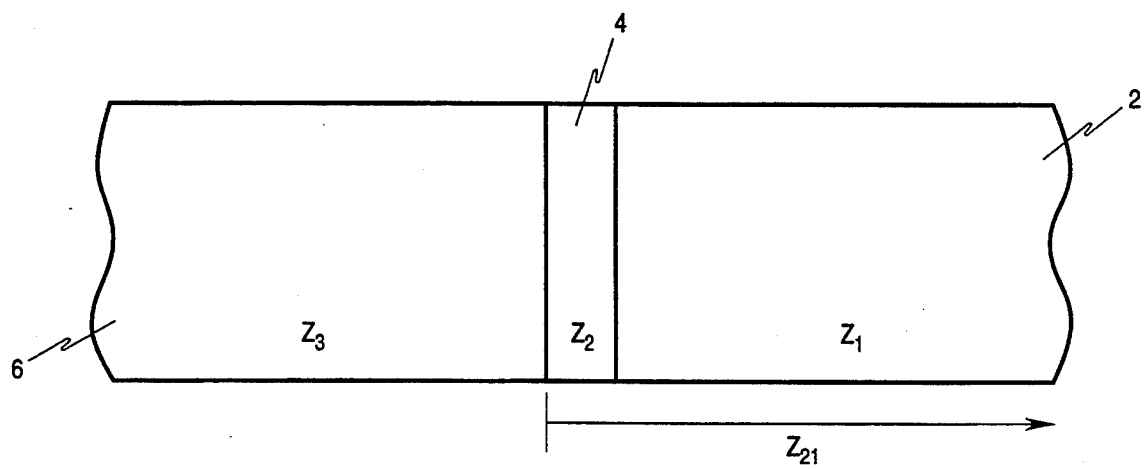
FIG. 1 illustrates a thin medium of acoustic impedance $Z_2$, sandwiched between two semi-infinite media such that the third (left most) medium sees the composite system formed by the first and second mediums as having an input acoustic impedance of $Z_{21}$.

Referring to FIG. 1, consider a first semi-infinite medium 2, with acoustic impedance $Z_1$, as depicted in FIG. 1. If a thin layer of a second medium 4, with acoustic impedance $Z_2$, is placed in contact with the left side of the first medium, the input impedance of the composite system (first medium + second medium ) is given by the complex relation:

$$Z_{21} = \frac{Z_2 Z_1 \cos(x_2\beta_2) + j Z_2^2 \sin(x_2\beta_2)}{Z_2 \cos(x_2\beta_2) + j Z_1 \sin(x_2\beta_2)}, \tag{2}$$

where j is the imaginary index and for the second medium, $x_2$ is the thickness, $\beta_2 2\pi/\lambda_2$ is the propagation constant and $\lambda_2$ is the acoustic wavelength, G. S. Kino, Acoustic Waves: Devices, Imaging and Analog Processing, (Prentice-Hall, 1987), p. 12. It should be noted that in the derivation of Eqn. 2, a steady state condition (continuous plane wave stimulation of the system of frequency, f) was assumed. Wavelength is related to frequency according to the relation, $c = \lambda_2 f$, where c is the acoustic velocity (either shear or longitudinal) in Medium 2. Next, consider what happens when a third (semi-infinite) medium 6, is placed in contact with the left side of the second medium as is also depicted in FIG. 1. If medium 6 has the same acoustic impedance as that of the first medium, then the stress wave reflection coefficient R, is given by the relation:

$$R = \frac{Z_{21} - Z_1}{Z_{21} + Z_1},\qquad(3)$$

The coefficient of acoustic power transfer $P_T$, across medium 2 can now be calculated;

$$P_T = 1 - |R|^2 = \qquad(4)$$

$$\frac{4 Z_2^2 Z_1^2}{(Z_1^2 + Z_2^2)^2 \sin^2\left(\frac{2\pi x_2 f}{c}\right) + 4 Z_2^2 Z_1^2 \cos^2\left(\frac{2\pi x_2 f}{c}\right)},$$

where the substitution $\beta_2 = 2\pi f/c$ has been applied.

Figure 2:
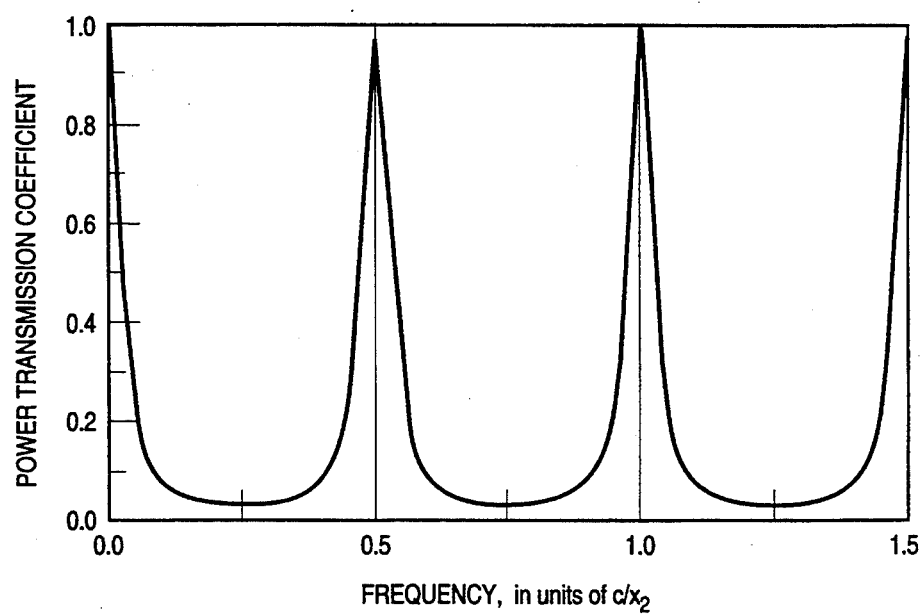
FIG. 2 illustrates the coefficient of acoustic power transmission across the second medium as a function of frequency for the three layer system depicted in FIG. 1, where $Z_1 = Z_3 = 17$ Rayls (Al) and $Z_2 = 1.48$ Rayls (water).

In FIG. 2, $P_T$ is plotted as a function of frequency for the case where the first and third media are aluminum ($Z_1 = 17$ Rayls) and the second medium is water ($Z_2 = 1.48$ Rayls). It can be seen that the condition of maximum power transmission occurs when $f = f_R = nc/2x_2$, where n is an integer. This behavior can be expected whenever $Z_2$ is higher than both $Z_1$ and $Z_3$ or lower than both $Z_1$ and $Z_3$ (as in this case). If $Z_2$ falls midrange between $Z_1$ and $Z_3$, maximum power transmission occurs when $f = f_R = (n+1) c/4x_2$. Note that the second medium was assumed to be lossless in the derivation of Eqn. 4. Taking attenuation into account, one would expect the amplitude of the local maxima to decrease with increasing n. The expression for Poisson's ratio (Eqn. 1) can now be rewritten as, $$\sigma = \frac{f_{Rl}^2 - 2f_{Rs}^2}{2f_{Rl}^2 - 2f_{Rs}^2},\qquad(5)$$

where $f_{Rs} \propto c_s/2x_2$ and $\overline{F}_{Rl} \propto c_l/2x_2$ are determined from the condition of maximum power transmission for shear and longitudinal acoustic waves, respectively.

EXPERIMENTAL TECHNIQUE

Figure 3:
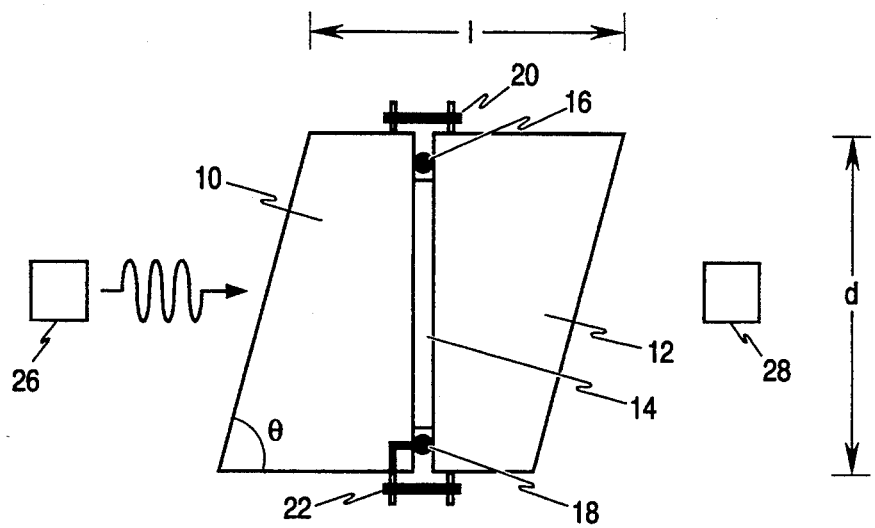
FIG. 3 is a top view of the experimental apparatus.

The experimental apparatus is depicted in FIG. 3. Two aluminum blocks 10, 12 are prepared from 1.5 inch square rod stock, each having a $\theta = 74°$ face and a 90° face with respect to one side of the block. A milled finish was determined to be adequate on the 74° faces. The 90° faces were lapped to insure that the surfaces were flat. A thin uniform layer of the specimen 14 being tested was sandwiched between the 90° faces. The spacing between these faces and hence, the specimen thickness, was determined by two identical, stainless steel wire spacers 16, 18. To hold this Al/specimen/Al sandwich together, small rubber O-rings 20, 22 was stretched over a set of threaded pegs located on each of two opposite sides of the sandwich as shown. The depth of thread for these pegs was less than 0.125 inches. The transducers and O-ring are bisected by a plane parallel to that of the page and 0.75 inches into sandwich. The approximate length 1 of the Al/specimen/Al sandwich is 1.75 inches. The dimension d is 1.5 inches, as the blocks were cut from square rod stock of 1.5 inch side.

The resultant AF specimen/Al sandwich was set upon a fixture (not shown) and submerged in a water tank (not shown) so as to be centered between a pair of 5 MHz, plane wave, through-transmission, ultrasonic transducers 26, 28. The 14 with respect to the transducers 26, 28. The apparatus is designed to approximate the conditions leading to the derivation of Eqn. 4. The Al blocks correspond to first and third media, the specimen to the second medium.

To perform measurements, one transducer 26 was stimulated to propagate a toneburst (single frequency) longitudinal drive pulse (water will not support a shear wave). The fixture was aligned so that this pulse would strike the first 74° face of the Al/specimen/Al sandwich at a particular angle of incidence $\theta_i$ to its normal, giving rise to both a longitudinal and a shear wave pulse within the aluminum, with angles of emergence $\theta_l$ and $\theta_S$, respectively. The emergence angles for a particular $\theta_i$ can be determined by the well known Snell's law analog, $$\frac{\sin \theta_i}{\sin \theta_s} = \frac{V_w}{V_s} \text{ and } \frac{\sin \theta_i}{\sin \theta_l} = \frac{V_w}{V_l}.\qquad(6)$$

where $V_w$ is the acoustic velocity in water, and $V_s$ and $V_l$ are the acoustic velocities for shear and longitudinal waves in aluminum, respectively.

Figure 4A:
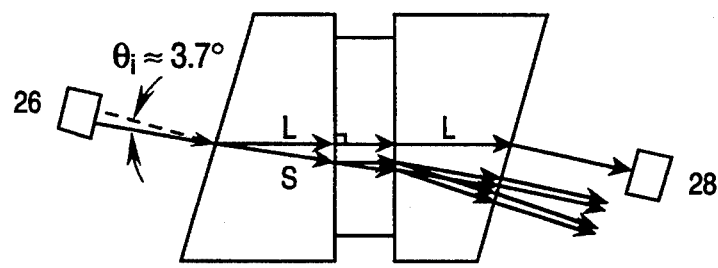
FIGS. 4A and 4B illustrate ray diagrams for the apparatus depicted in FIG. 3 where the specimen thickness has been enlarged for clarity.

In the first phase of the experiment illustrated in FIG. 4A, $\theta_i i$ was set at $\sim 3.7°$ so that the longitudinal pulse L transmitted through the first 74° face would strike the Al-specimen interface at normal incidence, and then travel through the remainder of the Al/specimen/Al sandwich to produce a signal at the receive transducer 28 as depicted in FIG. 4a. This signal will be referred to as the longitudinal response. Because the longitudinal velocity in Al exceeds that of the shear, the longitudinal response was the first signal detected after each drive pulse. This first signal was followed by others due to the shear waves transmitted through the first 74° face and various internal reflections within the sandwich. The duration of the drive pulse was chosen to be $\sim 1.5$ $\mu$s, which was short enough to permit temporal separation of the various signals, yet long enough to allow reverberations within the thin specimen layer to approximate a steady state (i.e., these reverberations did not significantly affect the lengths of the pulses). The amplitude of the longitudinal response was measured as a function of frequency (between 2 and 8 MHz). To isolate the effect of the specimen, the Al/specimen/Al sandwich was then replaced with a solid Al block of the same dimensions and the measurement repeated. This second set of data was divided into the first. The resultant data set was then normalized and plotted. Peaks in the the amplitude rs. frequency plot, which in accordance with Eqn. 4, occur when $f = f_{Rl} = nc_l/2x_2$ were then used to determine $c_l$, the longitudinal acoustic velocity of the specimen.

Figure 4B:
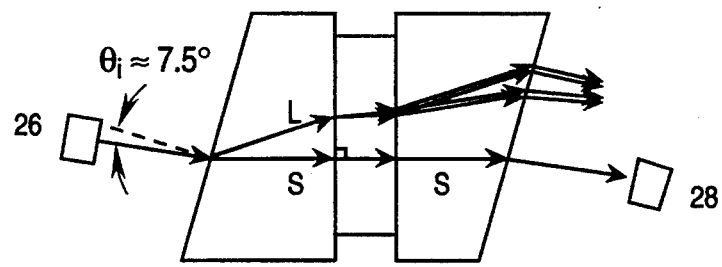

In the second phase of the experiment, illustrated in FIG. 4B, $\theta_i$ was set to $\sim 7.5°$, so that the direction of the transmitted shear waves was normal to the Al-specimen interface as depicted in FIG. 4B. The first signal resulting from this normal shear pulse will be referred to as the shear response. Following each drive pulse, the shear response was preceded by not only the longitudinal response, but also other signals resulting from internal reflections involving the faster longitudinal pulse L. To positively identify the shear response, one could increase $\theta_i$ beyond the critical angle for longitudinal wave production in the aluminum, so that the shear response would be the first remaining signal. One could then track this signal while decreasing $\theta_i$ to the appropriate value. The frequency dependence of the shear response amplitude was then measured, normalized and plotted in the same manner as that of the longitudinal response amplitude. Peaks in this plot, occurring when $f=f_{RS}=nc_s/2x_2$, were then be used to determine the shear acoustic velocity of the specimen, $c_s$.

RESULTS

Figure 5:
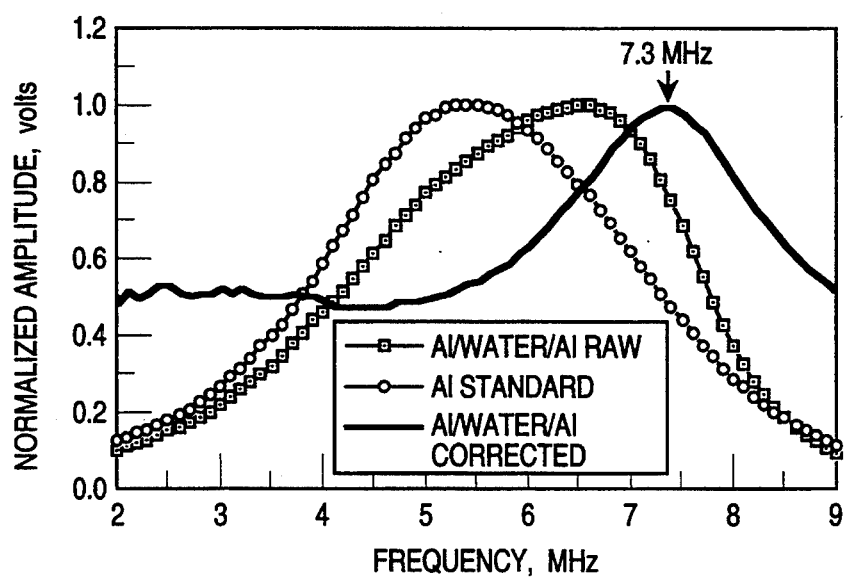
FIG. 5 is a graph of sample data for an Al/H$_2$O/Al sandwich, where the circles result from a measurement of the frequency response of a solid aluminum standard of the same dimensions as the sandwich.

Before attempting to measure both $c_s$ and $c_1$ in a material, a simpler system having no shear response was tested. An Al/H$_2$O/Al sandwich with wire spacers of diameter $x_2=1.016\times10^{-4}$ m (4 mil) was prepared. It should be emphasized that in this case (and all that follow), the 90° faces on the Al blocks were lapped flat with 600 grit garnet. Earlier tests, using blocks which had not been lapped, yielded results which were not satisfactory. In FIG. 5, the frequency response of the Al/H$_2$O/Al sandwich and a solid Al standard are plotted as boxes and circles, respectively. The second plot was divided into the first and normalized to produce the solid curve. The importance of this correction (for the transducer response and attenuation in the Al) is obvious as the peak shifts significantly from its position in the raw data. The peak in the solid curve, at $f_R=7.3$ MHz, was used to calculate $c_1=2f_{r1}x_2=1483$ m/s for water in excellent agreement with the literature value.

Figures 6A, 6B:
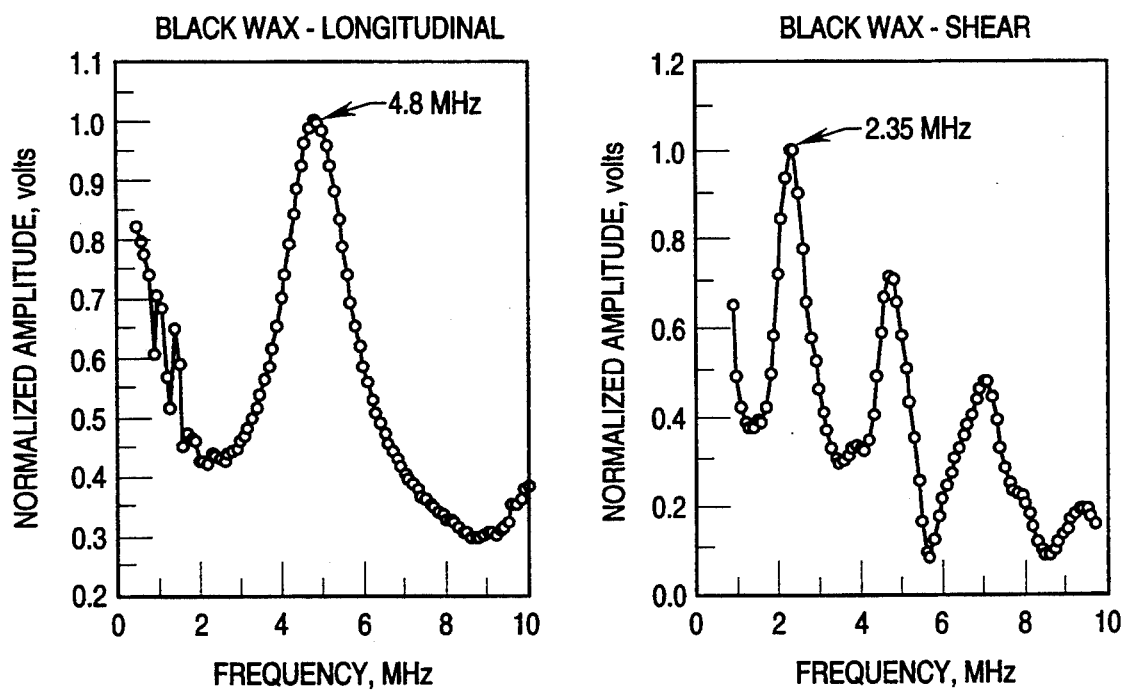
FIGS. 6A and 6B illustrate longitudinal and shear response data for a thin Black Wax specimen.

Three materials, Black Wax (BW), Five Minute Epoxy (FME) and Crystalbond (CB) adhesive, were selected for measurement of both $c_s$ and $c_1$. These materials were easily obtained and could be easily formed into both a thin specimen, as needed for this experiment, and a thick specimen for comparative purposes. The longitudinal response and shear response data for the thin Black Wax specimen are plotted in FIG. 6A and 6B. The raw data was corrected as outlined above to produce these curves. The wire spacers used for the Al/BW/Al sandwich were of diameter $2.39\times10^{-4}$ m (9.4 mils). The longitudinal response in FIG. 6A exhibits a peak at 4.8 MHz, corresponding to a longitudinal velocity of 2290 m/s. The shear response curve in FIG. 6B exhibits four equally spaced peaks, corresponding to $n=1, 2, 3$ and 4 in the relation; $f_{RS}=nc_s/2x_2$. As expected, the amplitude of these peaks decreases with increasing n, due to attenuation within the black wax. It should be noted that the data become less reliable as one pushes the limits on the operating range of the transducer (see the Al Standard plot of FIG. 5). The positions of the shear peaks correspond to a shear velocity of $c_s=1120$ m/s. As mentioned earlier, a thick specimen of black wax was also prepared of approximate dimensions, $2.5\times2.5\times0.66$ cm. The longitudinal and shear velocities of this specimen were measured using a standard through-transmission, ultrasonic technique. The values thus obtained are compared to those for the thin specimen in Table 1, along with similar results which were obtained for Crystalbond adhesive and Five Minute Epoxy. The entrees for Poisson's ratio were calculated using Eqn. 5.

DISCUSSION

It can be observed that for the three materials tested, the resonance technique for thin specimens described above leads to values for $c_1$, $c_s$ and Poisson's Ratio $\sigma$ which compare well with those determined using thicker specimens and a conventional through-transmission ultrasonic method (Table 1), differing by only a few percent. This difference falls within the uncertainty ascribed to the conventional measurement. When used to measure the acoustic velocity of water, the resonance technique yielded a value essentially equivalent to that reported in the literature. Sources of error for the resonance technique include error in determination of the resonant frequency, wire thickness and sample alignment, or nonuniformities in the specimen thickness which lead to a broadening of the resonance. The resonant frequency can be determined more accurately by sampling more points. Problems with specimen alignment can be mitigated through a well designed apparatus and careful experimentation. The wire thickness is important for determination of the velocities, but drops out of the equation for the Poisson's ratio.

The resonance technique presented should prove particularly useful for measurement of the mechanical properties of materials which exist (perhaps only) as thin (subwavelength) layers such as adhesives or highly attenuative materials. The use of a fluid couplant medium provides for uniform and repeatable coupling of the sound into the specimen. The capability for measuring both velocities on a single sample becomes especially useful when multi-component polymer systems are being tested, because of the variations within and between batches. In addition to the Poisson's ratio and acoustic velocities, if the density, p of the specimen is known, the Young's, shear and bulk moduli, E, $\alpha$ and K, can also be calculated via the familiar relations, $$E = \frac{\rho c_l^2(1-2\sigma)(1+\sigma)}{1-\sigma}; \quad \mu = \rho c_s^2 \text{ and } K = \frac{E}{3(1-2\sigma)}. \tag{7}$$

It is implicit that the properties measured are dynamic. In many instances, however, the temperature of the specimen and/or the frequency of measurement can be arranged so that the measurement occurs above or below the glass transition.

TABLE 1

Comparison of velocities measured for thin and thick specimens.

| Sample | $c_l$ ($10^5$ cm/s) | | $c_s$ ($10^5$ cm/s) | | $\sigma$ | |
|---|---|---|---|---|---|---|
| | Thin | Thick | Thin | Thick | Thin | Thick |
| BW | 2.29 | 2.23 | 1.12 | 1.11 | 0.364 | 0.355 |
| CB | 2.33 | 2.3 | 1.12 | 1.15 | 0.350 | 0.333 |
| FME | 2.7 | 2.7 | 1.25 | 1.28 | 0.343 | 0.335 |

In addition to the aforementioned applications, a number of enhancements and/or extensions of the technique can be envisioned. Instead of using a toneburst signal and sweeping the frequency, one might instead use a broadband pulse and Fourier transform the received signal. One could then effectively get all the information from a single pulse. The technique could also be arranged to study or monitor the cure of adhesives.

Although the invention has been described in terms of a preferred embodiment, it will be obvious to those skilled in the art that alterations and modifications may be made without departing from the invention. Accordingly, it is intended that all such alterations and modifications be included within the spirit and scope of the invention as defined by the appended claims.

We claim:

1. An apparatus disposed in an acoustic medium for measuring a first resonant frequency of a first longitudinal wave and for measuring a second resonant frequency of a second shear wave both acoustically resonating and propagating through a thin film, said apparatus comprising, a rectangular block of a predetermined material divided into first and second halves along a diagonal at an angle defining first and second diagonal sides respectively opposing first and second flat sides respectively of said first and second halves, said thin film being disposed between said first and second flat sides, said thin film having a thickness, said first and second diagonal sides facing away at said angle from said thin film and said first and second flat sides, a transmitter means for generating a first acoustic wave at a first incident angle offset from normal incidence to said first diagonal side, and for generating a second acoustic wave at a second incident angle offset from normal incidence to said first diagonal side, said first acoustic wave generating a first shear wave and said first longitudinal wave, said second acoustic wave generating said second shear wave and a second longitudinal wave, said second shear wave and said first longitudinal wave propagating from said first diagonal side, through said first halve, orthogonally through said thin film, through said second halve, and to said second diagonal side, a receiver means for sensing said first longitudinal wave and said second shear wave propagating from said second diagonal side, and processing means connected to said receiver means for determining said first resonant frequency of said first longitudinal wave through said thin film and for determining said second resonant frequency of said second shear wave through said thin film.

2. The apparatus of claim 1 further comprising
a spacer means disposed between said first and second flat side for defining a distance between said first and second halves equal to said distance.

3. The apparatus of claim 1 wherein
said predetermined material is aluminum,
said acoustic medium is water,
said diagonal angle is 74 degrees relative to said first and second flat sides,
said first incident angle is 3.7 degrees relative to a surface normal of said first diagonal side,
said second incident angle is 7.5 degrees relative to said surface normal of said first diagonal side, and
said processing means is a programmed computer.

4. The apparatus of claim 1 further comprising
a means for securing said first and second halves to opposing sides of said thin film respectively buttressing said first and second flat sides for forming a sandwich structure of said first halve, said thin film and said second halve.

5. The apparatus of claim 1 wherein
said processor means is for determining a longitudinal velocity for said thin film for said first longitudinal wave as a function of said first resonant frequency and said thickness, and for determining a shear velocity for said thin film for said second shear wave as a function of said second resonant frequency and said thickness.

6. The apparatus of claim 1 wherein
said processor means is for further determining Poisson's Ratio of said thin film as a function of said first and second resonant frequencies.

7. The apparatus of claim 1 wherein,
said first and second diagonal sides are facing away from each other and are parallel to each other.

8. The apparatus of claim 1 wherein said apparatus further comprises
a parallel piped formed of a first and a second parallel piped halves identical to said first and second halves when formed integrally together without said thin film disposed therebetween,
said processor means for further measuring a test longitudinal wave frequency response of said parallel piped from a test longitudinal wave identical to said first longitudinal wave, and
said processor means for further measuring a test shear wave frequency response of said parallelepiped from a test shear wave identical to said second shear wave.

9. The apparatus of claim 8 wherein
said processor means is for further determining Poisson's Ratio of said thin film as a function of said first and second resonant frequencies,
said first resonant frequency is determined from a quotient of a longitudinal wave frequency response of said first longitudinal wave propagating through said first and second halves with said thin film disposed therebetween divided by said test longitudinal wave frequency response of said parallelepiped, and
said second resonant frequency is determined from a quotient of a shear wave frequency response of said second shear propagating through said first and second halves with said thin film disposed therebetween divided by said test shear wave frequency response of said parallelepiped.

10. The apparatus of claim 1 wherein
said first and second acoustic waves are tone burst signals having varying frequencies, and
said first and second resonant frequencies are respectively determined by discrete sensing of signal amplitudes at said varying frequencies of said longitudinal and shear waves sensed by said receiver.

11. The apparatus of claim 1 wherein
said first and second acoustic waves are broadband pulses, and
said first and second resonant frequencies are respectively determined by Fourier transforms of said longitudinal and shear waves sensed by said receiver.

12. A method for measuring a first resonant frequency of a longitudinal wave and a second resonant frequency of a shear wave both acoustically resonating and propagating through a thin film, said method comprising the steps of,
dividing a rectangular block into a first halve and a second halve along a diagonal at an angle defining a first diagonal side and a second diagonal side respectively opposing a first flat side and a second flat side respectively of said first and second halves,
disposing said thin film between said first and second halves and buttressing said first and second flat sides, said diagonal sides facing away at said angle from said thin film and from said first and second flat sides, said thin film having a thickness separating said first and second flat sides in parallel relation to each other, generating a first acoustic wave at a first incident angle offset from normal incidence to said first diagonal side, said first acoustic wave generating said first longitudinal wave propagating from said first diagonal side, through said first halve, orthogonally through said thin film, through said second halve, and to said second diagonal side, sensing said longitudinal wave after propagating through said first halve, said thin film and said second halve, determining said first resonant frequency of said longitudinal wave in said thin film, generating a second acoustic wave at a second incident angle offset from normal incidence to said first diagonal side, said second acoustic wave generating said shear wave propagating from said first diagonal side, through said first halve, orthogonally through said thin film, through said second halve, and to said second diagonal side, sensing said shear wave after propagating through said first halve, said thin film and said second halve, and determining said second resonant frequency of said shear wave in said thin film.

13. The method of claim 12 further comprising the steps of,
determining a longitudinal velocity of said thin film as a function of said thickness and said first resonant frequency, and
determining a shear velocity of said thin film as a function of said thickness and said second resonant frequency.

14. The method of claim 12 further comprising the step of,
determining Poisson's Ratio as a function of said first and second resonant frequencies.

15. The method of claim 12 wherein said method further comprises the steps of,
lapping said first and second flat side to perfect flattening for providing a uniformity of said thickness of said thin film,
inserting a spacer between said first and second flat side to define said thickness of said thin film,
positioning said first and second diagonal side in parallel relation to each other, and
securing together said first halve, said thin film and said second halve into a sandwich structure.

16. The method of claim 12 further comprising the steps of,
storing a first frequency response of said longitudinal wave for said first and second halves with said thin film disposed therebetween,
storing a second frequency response of said shear wave for said first and second halves and said thin film disposed therebetween,
making a parallelepiped of identical size and material to said first and second block halves integrally formed together without said thin film disposed therebetween, said parallelepiped also having first and second parallelepiped diagonal sides,
generating said first acoustic wave at said first incident offset angle towards said first parallelepiped diagonal side, said first acoustic wave generating said longitudinal wave propagating through said parallelepiped to said second parallelepiped diagonal side,
sensing said longitudinal wave after propagating through said parallelepiped,
storing a first parallelepiped frequency response of said longitudinal wave for said parallelepiped,
generating said second acoustic wave at said second incident offset angle towards said first parallelepiped diagonal side, said second acoustic wave generating said shear wave propagating through said parallelepiped to said second parallelepiped diagonal side,
sensing said shear wave after propagating through said parallelepiped, and
storing a second parallelepiped frequency response of said shear wave for said parallelepiped.

17. The method of claim 16 wherein,
said first resonant frequency is determined by dividing said first parallelepiped frequency response into said first frequency response resulting in a thin film longitudinal wave frequency response having a peak amplitude at said first resonant frequency, and,
said second resonant frequency is determined by dividing said second parallelepiped frequency response into said second frequency response resulting in a thin film shear wave frequency response having a peak amplitude at said second resonant frequency.

18. The method of claim 17 wherein,
each of said first and second acoustic waves are a series of pulses having respective monotonic frequencies, and
said first and second resonant frequencies are determined by discrete sensing of signal amplitudes of said first parallelepiped frequency response, said first frequency response, said second parallelepiped frequency response and said second frequency response at discrete ones of said monotonic frequencies.

19. The method of claim 17 wherein,
each of said first and second acoustic waves are a broadband pulse having broadband frequencies, and
said first and second resonant frequencies are determined by Fourier transforms of said first parallelepiped frequency response, said first frequency response, said second parallelepiped frequency response and said second frequency response over said broadband frequencies.

20. A method for determining Poisson's Ratio of a thin film, said method comprising the steps of,
dividing a rectangular block into a first halve and a second halve along a diagonal at an angle defining a first diagonal side and a second diagonal side respectively opposing a first flat side and a second flat side respectively of said first and second halves,
disposing said thin film between said first and second halves and buttressing said first and second flat sides, said diagonal sides facing away at said angle from said thin film and from said first and second flat sides, said thin film having a thickness separating said first and second flat sides in parallel relation to each other,
generating a first acoustic wave at a first incident angle offset from normal incidence to said first diagonal side, said first acoustic wave generating a first longitudinal wave propagating from said first diagonal side, through said first halve, orthogonally through said thin film, through said second halve, and to said second diagonal side, sensing said longitudinal wave after propagating through said first halve, said thin film and said second halve, storing a first frequency response of said longitudinal wave for said first and second halves with said thin film disposed therebetween, generating a second acoustic wave at a second incident angle offset from normal incidence to said first diagonal side, said second acoustic wave generating a shear wave propagating from said first diagonal side, through said first halve, orthogonally through said thin film, through said second halve, and to said second diagonal side, sensing said shear wave after propagating through said first halve, said thin film and said second halve, storing a second frequency response of said shear wave for said first and second halves and said thin film disposed therebetween, making a parallelepiped of identical size and material to said first and second block halves integrally formed together without said thin film disposed therebetween, said parallelepiped also having first and second parallelepiped diagonal sides, generating said first acoustic wave at said first incident offset angle towards said first parallelepiped diagonal side, said first acoustic wave generating said longitudinal wave propagating through said parallelepiped to said second parallelepiped diagonal side, sensing said longitudinal wave after propagating through said parallelepiped, storing a first parallelepiped frequency response of said longitudinal wave for said parallelepiped, generating said second acoustic wave at said second incident offset angle towards said first parallelepiped diagonal side, said second acoustic wave generating said shear wave propagating through said parallelepiped to said second parallelepiped diagonal side, sensing said shear wave after propagating through said parallelepiped, storing a second parallelepiped frequency response of said shear wave for said parallelepiped, determining said first resonant frequency by dividing said first parallelepiped frequency response into said first frequency response resulting in a thin film longitudinal wave frequency response having a peak amplitude at said first resonant frequency, determining said second resonant frequency by dividing said second parallelepiped frequency response into said second frequency response resulting in a thin film shear wave frequency response having a peak amplitude at said second resonant frequency, and determining Poisson's Ratio as a function of said first and second resonant frequencies.

* * * * *